United States Patent [19]

Dinh et al.

[11] Patent Number: 6,018,679
[45] Date of Patent: *Jan. 25, 2000

[54] IONTOPHORETIC TRANSDERMAL DELIVERY AND CONTROL OF ADVERSE SIDE-EFFECTS

[75] Inventors: Steven Minh Dinh, Briarcliff Manor; Parminder Bobby Singh, Suffern; Ann Reese Comfort, New City, all of N.Y.

[73] Assignee: Novartis Finance Corp., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/791,787

[22] Filed: Jan. 29, 1997

[51] Int. Cl.[7] ............................................. A61N 1/30
[52] U.S. Cl. .................................... 604/20; 604/501
[58] Field of Search ......................... 604/20, 501, 314; 128/760; 600/573; 424/449

[56] References Cited

U.S. PATENT DOCUMENTS

| | | |
|---|---|---|
| 4,141,359 | 2/1979 | Jacobsen et al. . |
| 4,301,794 | 11/1981 | Tapper . |
| 4,340,047 | 7/1982 | Tapper et al. ............................. 128/207 |
| 4,383,529 | 5/1983 | Webster .................................... 604/20 |
| 4,406,658 | 9/1983 | Lattin et al. .............................. 604/20 |
| 4,416,274 | 11/1983 | Jacobsen et al. ......................... 604/20 |
| 4,744,787 | 5/1988 | Phipps et al. ............................. 604/20 |
| 4,747,819 | 5/1988 | Phipps et al. ............................. 604/20 |
| 4,752,285 | 6/1988 | Petelenz et al. .......................... 604/20 |
| 4,764,164 | 8/1988 | Sasaki ....................................... 604/20 |
| 4,915,685 | 4/1990 | Petelenz et al. .......................... 604/20 |
| 5,006,108 | 4/1991 | LaPrade ................................... 604/20 |
| 5,069,908 | 12/1991 | Henley .................................... 421/449 |
| 5,087,242 | 2/1992 | Petelenz et al. .......................... 604/20 |
| 5,133,972 | 7/1992 | Ferrini et al. ............................. 424/449 |
| 5,135,477 | 8/1992 | Untereker et al. ........................ 604/20 |
| 5,224,927 | 7/1993 | Tapper ..................................... 604/20 |
| 5,236,412 | 8/1993 | Lloyd et al. .............................. 604/20 |
| 5,279,543 | 1/1994 | Glikfeld et al. .......................... 604/20 |
| 5,281,287 | 1/1994 | Lloyd et al. .............................. 156/80 |
| 5,286,252 | 2/1994 | Tuttle et al. .............................. 604/20 |
| 5,286,254 | 2/1994 | Shapland et al. ......................... 604/20 |
| 5,320,597 | 6/1994 | Sage, Jr. et al. .......................... 604/20 |
| 5,328,455 | 7/1994 | Lloyd et al. .............................. 604/20 |
| 5,374,241 | 12/1994 | Lloyd et al. .............................. 604/20 |
| 5,415,628 | 5/1995 | Untereker et al. ........................ 604/20 |
| 5,582,586 | 12/1996 | Tachibana et al. ....................... 604/20 |
| 5,730,715 | 3/1998 | Sage, Jr. et al. .......................... 604/20 |

FOREIGN PATENT DOCUMENTS

| | | |
|---|---|---|
| 0 483 883 | 5/1992 | European Pat. Off. . |
| 0 498 353 | 8/1992 | European Pat. Off. . |
| 0542294 | 5/1993 | European Pat. Off. . |
| 0547482 | 6/1993 | European Pat. Off. . |
| 92/17239 | 10/1992 | WIPO . |
| WO95/09032 | 4/1995 | WIPO . |

OTHER PUBLICATIONS

Wong, Drugs Pharm. Sci. (1994), 62, 219–46, (1994).

Singh et al., Critical Reviews in Therapeutic Drug Carrier Systems, 11 (2 & 3): 161–213 (1994).

Kasting and Keister, J. Membrance Sci., 35, 137–159, (1988).

Primary Examiner—Mark Bockelman
Attorney, Agent, or Firm—Gregory D. Ferraro

[57] ABSTRACT

A method is disclosed for iontophoretically removing any compound that is capable of causing skin irritation or other harmful effects. More specifically, a bipolar iontophoretic transdermal delivery method is disclosed that includes a reversal phase for controlling the iontophoretic transdermal delivery of pharmaceutical compounds while reducing or eliminating skin irritation and terminating the pharmacological or toxicological effects in skin of drugs/cosmetics/active ingredients which form a drug depot in the skin after passive or iontophoretic application.

12 Claims, 1 Drawing Sheet

IONTOPHORETIC TRANSDERMAL DELIVERY AND CONTROL OF ADVERSE SIDE-EFFECTS

FIELD OF THE INVENTION

The subject invention relates to a method for iontophoretically removing any compound that is capable of causing skin irritation or other harmful effects. More specifically, the subject invention relates to a method for controlling the iontophoretic transdermal delivery of pharmaceutical compounds while reducing or eliminating skin irritation and terminating the pharmacological or toxicological effects in skin of drugs/cosmetics/active ingredients which can form a drug depot in the skin after passive or iontophoretic application.

BACKGROUND OF THE INVENTION

The iontophoretic transdermal delivery of pharmaceutical compounds relates to introducing ions of soluble salts of therapeutic agents into tissues of the body under the influence of an applied electric field. Recent reviews have summarized the features and benefits of iontophoretic transdermal delivery systems as compared with passive transdermal systems as well as with other means of delivering drugs into the bloodstream, for example, O. Wong, "*Iontophoresis: Fundamentals*", in *Drugs Pharm. Sci.* (1994), 62 (*Drug Permeation Enhancement*), 219–46 (1994); and P. Singh et al., "*Iontophoresis in Drug Delivery: Basic Principles and Applications*", *Critical Reviews in Therapeutic Drug Carrier Systems*, 11(2&3):161–213 (1994). Thus, it is known that in certain cases when oral delivery of a particular drug may be ineffective or unacceptable because of poor GI absorption, extensive first pass effect or other side effects, transdermal delivery may provide an advantageous method of delivering such drugs. However, while topical delivery using passive transdermal delivery devices may provide an acceptable alternative in many cases, there are still certain circumstances when an adequate dose of the drug cannot be practically delivered due to inadequate migration rates, rather long lag times, cannot be practically delivered due to inadequate migration rates, rather long lag times, inter- and intra-patient flux variability, the need for unacceptably large transdermal patches and/or concentration levels of the drug that cause skin irritation effects. In some cases, an iontophoretic transdermal delivery system may be useful to overcome these types of difficulties.

Passive transdermal delivery has been reported of phosphate compounds, and in particular bisphosphonates, which are derivatives of methanediphosphoric acid, in U.S. Pat. No. 5,133,972 and iontophoretic delivery of etidronate, which is also a bisphosphonate drug, has been reported in Kasting and Keister (*J. Membrane Sci.,* 35, 137–159, 1988). These transdermal bisphosphonate delivery systems are intended to provide drug delivery methods which avoid or reduce the problems associated with oral delivery of bisphosphonate compounds. These compounds which are known to be useful for the treatment of Paget's disease, osteoporosis and bone metastases.

However, in passive transdermal delivery systems, the flux of the drug across skin is low and highly scattered because of the polarity of the delivered form of the drug over the range of pH values from 2 to 10. Since an iontophoretic delivery system uses an external electrical power source to control the transport of the drug across skin, the drug flux can be increased while simultaneously reducing the variability in its delivery. However, it has now been found that in the transdermal delivery of bisphosphonates, an unusual pattern of skin irritation is observed for in vivo studies in both passive and iontophoretic delivery systems. In particular, as distinct from the skin irritation that may be produced due to extremes in pH that occur in iontophoretic systems, for which preventive measures have been disclosed, such as in U.S. Pat. Nos. 4,915,685 or 5,224,927, a delayed onset of skin irritation, from a few days to a week, is typically observed after the transdermal bisphosphonate delivery system is removed from the skin to which it was attached. The level of irritation depends on the concentration of the, drug and, for the case of iontophoresis, also on the applied current. In addition to moderate to severe erythema and/or edema, white precipitates may also be observed. In mild cases, the skin may resolve after a period of time, typically 3 to 4 weeks. In severe cases, necrosis may form.

SUMMARY OF THE INVENTION

An object of the subject invention is to provide iontophoretic transdermal technology that is useful for removing any compound that is capable of causing skin irritation or other harmful effects.

More specifically, an object of the subject invention is to provide a bipolar iontophoretic transdermal technology that is useful for reducing delayed skin irritation effects that are caused by iontophoretically delivered pharmaceutical compounds.

Still more specifically, an object of the subject invention is to provide a method for reducing or eliminating the drug depot that is believed to be produced in the various layers of the skin by either passive or iontophoretic transdermal drug delivery systems and that is also believed to be the cause of delayed skin irritation effects or other unwanted pharmacological and/or toxicological effects in the skin and/or systemic circulation.

In particular, an objective of the subject invention is to reduce or remove the drug depot that is believed to be produced in the various layer of the skin, from either passive or iontophoretic transdermal drug delivery systems, by reversing the direction of current flow used to iontophoretically deliver the drug.

More particularly, the subject invention is directed to a uniphasic (or unipolar) iontophoresis for passive transdermal delivery systems and biphasic (or bipolar) iontophoretic method for reducing delayed skin irritation effects or other unwanted pharmacological and/or toxicological effects in the skin and/or systemic circulation that may be caused by transdermal bisphosphonate drug delivery systems.

DETAILED DESCRIPTION OF THE PREFERRED EMBODIMENTS

Figure 1:
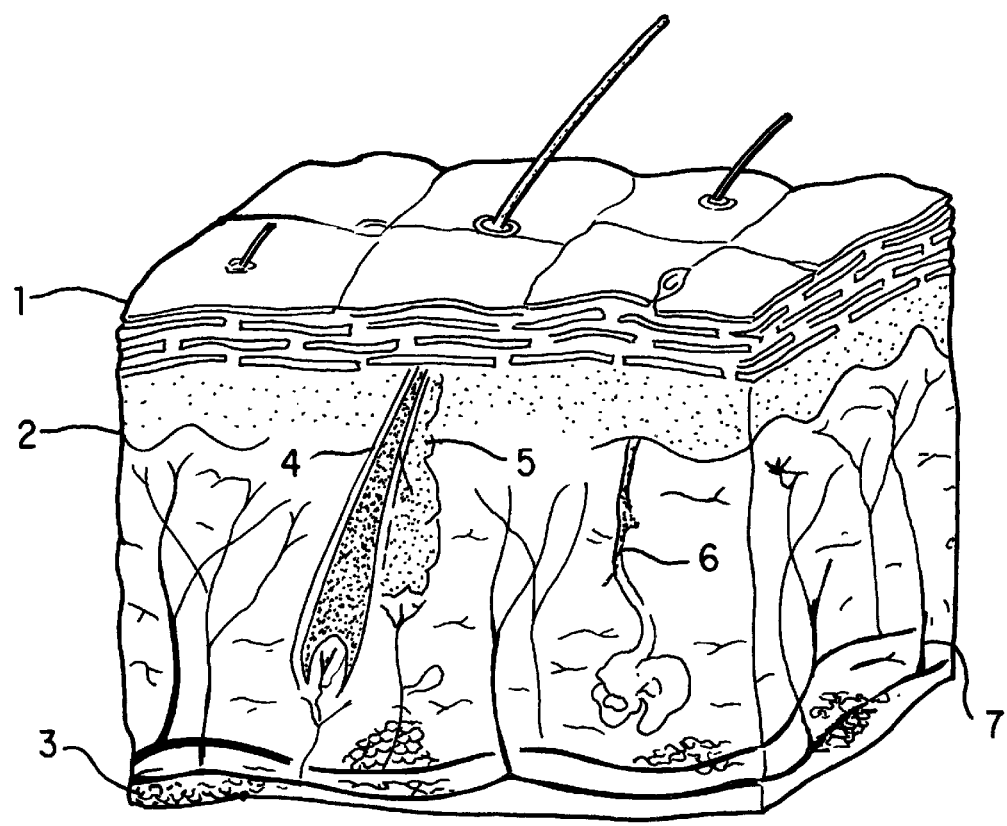
FIG. 1 shows the region of the skin surface wherein harmful drug depots may be formed during iontophoretic drug delivery.

The subject invention and preferred embodiments thereof are hereinafter disclosed so as to provide a detailed description of the invention without in any way intending to limit the subject invention to the specific embodiments disclosed herein.

The subject invention is based on the discovery that delayed skin irritation effects caused by transdermal delivery of bisphosphonate compounds can be substantially reduced by reversing the direction of the current flow used to iontophoretically deliver the drug. While the subject method is not to be limited by the theory of how the subject invention works, it is believed that a passive or iontophoretic transdermal system may produce a residual level of active therapeutic agent that remains in a drug depot in the different layers of the skin long after the drug delivery step is completed and the transdermal delivery system has been removed. In the case of bisphosphonate compounds, for example, it is believed that this depot (bound or unbound) contains drug that does not become absorbed into the blood circulation, and over a delay period of several days or more this drug can quite unexpectedly cause delayed onset of skin irritation effects. The subject method is, thus, directed to reducing or eliminating the skin irritation effects that may not become evident until a day or two, or even a week to ten days, after completion of the drug delivery step.

Surprisingly, it was found that by reversing the current flow of the iontophoretic delivery device after the delivery phase was completed, the skin irritation effects could be reduced or avoided. Thus, the current reversal is intended to be carried out at high enough current levels for long enough time intervals so as to effectively remove the residual levels of the unabsorbed bisphosphonate compounds from the drug depot. The overall method is, thus, referred to herein as a bipolar (or biphasic) iontophoresis process, which includes a delivery period for delivering the drug and a reversal period for removing drug still remaining in the drug depot. In the delivery period of the process, the iontophoretic transdermal delivery device provides an applied current to enhance and control the delivery of active ingredient and, in the reversal period after drug is absorbed by the systemic circulation, the drug still remaining in the skin and tissue layers are removed from the body by reversing the polarity of the applied voltage. Similarly, the reversed polarity, which causes net transport of drug out of the skin, may be used to reduce or eliminate skin irritation by removing the drug depot from an initial period of passive transdermal delivery.

Iontophoretic treatment methods, such as described in U.S. Pat. No. 4,301,794, have been disclosed in which current reversal is intermittently applied through the use of relatively short pulses of reversed current flow, typically having a pulse length of a few milli-seconds, as compared to a forward current having a duration controlled to be substantially longer, so as to control the ratio of the forward energy to the reverse energy within a prescribed range. Such intermittent iontophoretic delivery is intended to reduce skin irritation effects that are typically experienced concurrent with delivery of the drug, for example, such as iontophoretic burns caused by localized pH changes or still other unpleasant skin sensation phenomena.

The subject invention differs from these methods in that, inter alia, the subject method is directed toward reversing the current flow after iontophoretic delivery of a desired dosage of a particular drug, referred to herein as a unit dosage, so as to remove residual levels of drug that remain in the various layers of the skin after iontophoretic or passive delivery of the drug, wherein the skin irritation effects may not be detected until long after the iontophoretic or passive step is completed. A unit dosage of the drug refers to that amount which is delivered during a single treatment step. During the initial phase of providing the iontophoretic treatment, the applied voltage causes the concentration of the drug in the outermost layers of the skin to build up until a steady state concentration gradient is established between the outermost layer of the skin, which is in contact with the delivery patch, and the circulation system of the patient, which continuously carries drug away from this overall region. Referring to FIG. 1, which shows the epidermis 1, the dermis 2, subcutaneous fat 3, a hair follicle 4, a sebaceous gland 5, a sweat duct 6 and blood vessels 7, the drug depot sites may be found anywhere within the region extending from the epidermis region of the skin surface into the underlying regions, including the dermis region and at least as deep as the subcutaneous fat region.

Flow of drug downward along the concentration and electrical potential gradients, which extend from the skin surface to the underlying regions shown in FIG. 1 continues for as long as the applied voltage across the skin is present. However, upon terminating the applied voltage, there is no longer a driving force that promotes transport of the drug across this region of the skin toward the circulation system, and at this time some of the drug remains in the skin. The drug remaining in the skin may exist in equilibrium between bound and unbound drug, wherein some of the drug may even be irreversibly bound. In addition, polar compounds such as bisphosphonates may precipitate and remain in the lipid domains of the skin layers until sufficient time has elapsed for the drug molecules to redissolve. Depletion of drug from the skin depends on the desorption kinetics of the drug. If drug is allowed to remain in the depot for too long a period of time, significant skin irritation effects may gradually begin to appear, but possibly with a significant delay before onset of any symptoms, in contrast with those skin irritation effects that are encountered substantially concurrent with delivery of the drug. While the drug concentration gradient that is built up at the skin surface during the delivery phase may serve a necessary function during drug delivery, the drug remaining in this region may need to be removed under certain circumstances. In particular, for those drugs that cause significant irritation or other unwanted pharmacological and/or toxicological effects, if allowed to remain in the skin for an extended period of time, the subject method may be used to reduce or eliminate such effects. Such is the case, for example, for bisphosphonate compounds.

The delivery period may be described as comprised of two phases, the initial phase in which a steady state concentration gradient of the drug is built up at the skin surface before significant transport of the drug to systemic circulation can occur, and a transport phase in which a major fraction of the drug is actually transported from the surface of the skin deep enough into the interior to be carried away by systemic circulation. The transport phase is typically carried out for as long as necessary to provide the desired dosage of the drug.

Since the reversal period only requires removal of drug from the depot, the total electrical energy provided during the delivery period may be different from the total electrical energy provided during the reversal period. However, since somewhat longer reversal periods may be desired under certain circumstances, for example, so as to thoroughly flush substantially all of a particularly active drug from the depot, the subject invention is not limited only to having delivery periods that are substantially longer than the reversal period. In any case, the actual energy, as determined by the length of time and current flow, that is used during the reversal period for a particular drug is determined, in general, to be that which is necessary to reduce or eliminate the delayed skin irritation or other unwanted pharmacological and/or toxicological effects.

Iontophoretic delivery of drug compounds generally comprises a drug delivery treatment protocol that includes periodically applying an iontophoretic transdermal patch at intervals that may be as frequent as twice daily or as infrequent as once a week or once a month. Typically, in what is herein referred to as a single treatment step, the patch is applied, the drug is iontophoretically delivered and the patch is then removed, with another patch being applied again, typically at a different site, when the next treatment step is due to be carried out. Although the absolute quantity of the drug delivered may vary substantially, a unit dosage is herein defined to be that quantity of drug, however large or small, that is delivered during a single treatment step by a single patch application at an individual site. Since the objective of the reversal period is to remove drug from the different layers of the skin, this means that the reversal period reduces the surface-layer concentration of the drug that provides the driving force, together with the applied voltage, for delivering drug. Since the surface-layer concentration would need to be replenished, if delivery of the drug compound were to resume once again immediately after the reversal period, and since the subject invention is directed toward reducing or eliminating those skin irritation effects that are caused by drug remaining in the drug depot for a substantial length of time after the treatment step is completed, the subject invention is directed to a process in which the reversal current is not provided until after a unit dosage of the drug compound is delivered at an individual site. Since another patch may be applied to a different site so as to deliver the next dosage in a manner according to a continuous regimen, drug removal from the depot at the first site may be carried out even while additional drug is being delivered to the new site.

The subject method is, thus, specifically directed toward eliminating skin irritation effects that have a delayed onset. However, it is to be understood that the subject method may be used in combination with methods that are intended for preventing or reducing those skin irritation effects that are typically observed concurrent with delivery of the drug.

Although the subject method was discovered in an attempt to iontophoretically deliver therapeutic dosages of bisphosphonate compounds in a manner so as to avoid the delayed skin irritation effects discovered to be caused by such compounds, the invention may also be used for other transdermally delivered drug compounds that produce delayed skin irritation or other pharmacological or toxicological effects. In particular, the subject drug removal method may be used for passive transdermal delivery methods as well as for iontophoretic delivery methods.

In fact, the subject invention relates to the materials and methods that are useful for iontophoretically removing any compound that is capable of causing skin irritation or other harmful or injurious effects. Thus, although the type of harm or injury contemplated for the representative embodiment disclosed herein relating to a bipolar iontophoretic drug delivery method relates to the delayed skin irritation effects that may be caused by pharmacological compounds that are purposefully introduced because of their beneficial effects, it is also contemplated that-the subject invention may be used to remove inherently harmful or injurious compounds which may behave as irritants and which may be accidentally spilled on the body or invasively introduced into the body, such as by insects or other poisonous species.

Since an iontophoretic delivery method typically delivers the drug by making use of some type of patch, which is impregnated with the drug, the same patch may also be used during the reversal period to remove the drug that remains in the drug depot. Alternatively, it is possible that under certain circumstances when the drug is iontophoretically delivered, a separate patch may be desirable for use during the reversal period. Whenever the drug is delivered by passive means, whether through use of a passive transdermal delivery patch or by application of an ointment, jelly, cream, lotion, powder, emulsion, sunscreen, etc., a patch capable of causing iontophoretic removal of the drug may be applied after the passive delivery period.

An iontophoretic removal patch would not necessarily include a pharmaceutical compound or still other compounds that are typically intended for delivery into a targeted body, but might well include solvents or other materials that are specifically selected to enhance removal and effective up-take of the harmful or injurious compound into the removal patch. In those cases wherein the iontophoretic transdermal patch is intended to be used primarily or solely to remove an irritant, the iontophoretic transdermal "removal" patch may differ from a typical iontophoretic drug delivery patch in that the removal patch may not contain any drug or active ingredient, except that, under certain circumstances, the removal patch may contain an "anti-irritant" which is to be delivered while the irritant is being removed. The electrolyte in the removal patch may typically be NaCl, KCl, $CaCl_2$, $MgCl_2$, etc., inorganic or organic buffers (pH 2–9); wherein the proper selection of buffer, pH and ionic strength is determined by the particular compound being removed.

The iontophoretic drug delivery process typically involves applying a voltage across two electrodes on the skin so as to cause current to flow between the electrodes, wherein a part of the current is carried by ionic species of the drug compound. During both the delivery period as well as the reversal period, the current may be caused to flow by applying a constant, pulsed or alternating voltage. When an alternating current is employed, the duty cycle may be adjusted during the delivery and reversal periods to achieve the desired balance between enhancing drug delivery and reducing the side-effects caused by prolonged drug deposition in the skin layers.

The pulsed or alternating voltage may have a frequency from about 1 Hz to about 100 MHz using substantially any type of waveform shape, including sine, square, triangular, sawtooth, rectangular, etc. In addition, the pulsed or alternating voltage may be applied on a duty cycle less than 100%.

The electrolyte composition during the reversal period, as well as during the delivery period, may contain univalent or divalent ions, for example, NaCl, $CaCl_2$ (0–M), etc., including commonly used buffers having a pH of 2–10.

In summary, the subject method is based on the general discovery that effective removal of the drug depot that does not become absorbed by systemic circulation can substantially reduce or eliminate delayed skin irritation or other unwanted pharmacological and/or toxicological effects.

Insofar as the subject invention is to be directed toward reducing or eliminating the delayed skin irritation effects of bisphosphonate compounds, the bisphosphonate compounds may comprise any of a broad range of compounds such as disclosed in U.S. Pat. No. 5,133,972, which is herein incorporated in its entirety by reference. In particular, the bisphosphonate compound is a pharmaceutically acceptable methanediphosphonic acid derivative of formula ($R_1C(PO_3H_2)_2R_2$) or a salt thereof.

Insofar as the subject invention is to be directed toward reducing or eliminating the delayed skin irritation effects of other types of compounds, the other compounds may be comprised of substantially any type of compound that may be transdermally delivered, for example, by application of a transdermal patch, an ointment, jelly, cream, lotion, powder, emulsion, sunscreen, etc., and then removed by an iontophoretic removal process. For example, the compounds for which the subject invention may be used include, corticosteroids, antifungals, antibacterials, muscle relaxants, cosmetics, trace metal ions, antihypertensive, beta-blockers, anticancer, peptide-based drugs, oligonucleotides, etc.

The iontophoretic systems used to practice the subject invention may include devices and/or components selected from a wide variety of commercially available devices or components and/or from a wide range of methods and materials such as taught, for example, by the patents and publications relating to such iontophoretic systems. In particular, the iontophoretic transdermal system may comprise a iontophoretic device such as is available from Iomed of Salt Lake City, Utah, the IOMED™ model PM700 phoresor II, or a device such as manufactured by Empi of St. Paul, Minn., the Empi DUPEL™, or a device known as the LECTRO™ Patch, such as manufactured by General Medical Device Corp. of Los Angeles, Calif.

The electrodes may be comprised of reactive or non-reactive electrodes. Examples of reactive electrodes are those made from metal salts, such as silver chloride or materials described in U.S. Pat. No. 4,752,285. The silver chloride electrodes are available from Iomed. Alternative reactive electrodes can be made from a combination of ion-exchange resins, such as the electrodes available from Empi. Examples of non-reactive electrodes are those made from metals such as gold or platinum, or from carbon particles dispersed in polymeric matrices such as one used in the LECIRO™ Patch.

The adhesives may be comprised of pressure sensitive adhesives used in passive transdermal delivery systems, such those derived from silicone or acrylic polymers, or those derived from rubbers such as polyisobutylene. A combination of pressure sensitive and conductive adhesive can also be used, such as those described EPA 0 542 294.

The reservoir gels may be comprised of water soluble polymers or hydrogels, such as polyvinyl alcohol, or crosslinked hydrogels described in U.S. Pat. 5,069,908.

The devices or methods for reducing skin irritation and sensation may be comprised of still other methods and materials, such as described in WO 92 17239, EPA 0 547 482, U.S. Pat. No. 4,764,164. The technology of bipolar delivery has been disclosed in patents issued, or reported as pending, to General Medical Device Corp. and Advance Corp. of Tokyo, Japan.

The subject iontophoretic drug delivery method for reducing delayed onset of skin irritation typically comprises a direct/pulsed/alternating current flow of about 0.01 to about 4 $mA/cm^2$ during the delivery phase of the drug. A representative narrower range for the current flow may be from about 0.05 to about 2 $mA/cm^2$. A representative still narrower range for the current flow may be from about 0.1 to about 1 $mA/cm^2$.

The representative unit dosage that may typically be delivered during a single delivery period may vary in amount from about 1 ng to about 100 mg. The unit dosage that is delivered may be determined on the basis of a wide range of factors, including compound, condition, age, body weight, clearance, etc. A representative narrower range for the unit dosage may be from about 100 ng to about 75 mg. A representative still narrower range for the unit dosage may be from about 1 $\mu$g to about 50 mg.

The length of a representative time period for delivery of bisphosphonate compounds is typically from about 1 second to about 8 hours, wherein the delivery period may be from about 1 second to about 4 hours.

The subject method may typically comprise a reversed current flow that is at a level from about 0.01 $mA/cm^2$ to about 4 $mA/cm^2$. A representative narrower range for the reversed current flow may be from about 0.05 to about 2 $mA/cm^2$. A representative still narrower range for the reversed current flow may be from about 0.10 to about 1 $mA/cm^2$.

Typically the subject method comprises a reversal period that lasts long enough so as to remove substantially all drug remaining at the skin surface that is capable of causing delayed skin irritation or other unwanted pharmacological/toxicological effects.

In fact, each of these process conditions may be varied over a wide range, wherein the actual set of conditions selected may be determined by balancing a wide range of trade-offs.

In a representative embodiment of the subject method, iontophoretic delivery of a bisphosphonate compound is now described in more detail, wherein it is expressly understood that the materials, methods, compounds and conditions as recited herein are provided for illustrative purposes only, without any intention of limiting the claimed invention to the specific processes or conditions described hereinafter.

An Example of the Invention

A bisphosphonate compound, 2-(imidazol-1-yl)-1-hydroxyethane-1,1-bisphosphonic acid, was delivered-to test rabbits by impregnating a delivery patch with a drug solution of the bisphosphonate compound, attaching the patch to the test animals and delivering the compound to the test animals using conventional materials and techniques except that the power supply was a IOMED model PM700 phoresor II that was equipped to provide the current for drug delivery. The bipolar phase to remove the drug depot was accomplished by reversing the direction of the current manually.

A. An irritation study in rabbits following iontophoresis with bisphosphonate compound was conducted to evaluate dermal irritation.

The Group 1 animals (Control) received saline and a current setting of 240 $\mu$A for a 4 hour treatment period. Group 2 animals received 0.05 mg/ml bisphosphonate compound at 240 $\mu$A for 4 hours. The Group 3 animals received 0.1 mg/ml at 240 $\mu$A for 4 hours (total dose delivered=7.1 $\mu$g±0.35). Group 4 animals received 0.2 mg/ml at 240 $\mu$A for 4 hours (total dose delivered=22.5 $\mu$g±1.2). The Group 5 animals received 0.2 mg/ml at 480 $\mu$A for 2 hours (total dose delivered=30.2 $\mu$g±7.3). The Group 6 animals received 0.3 mg/ml at 100 $\mu$A for 4 hours. The Group 7 animals received 0.3 mg/ml at 0 $\mu$A for 4 hours. All animals received a single treatment followed by a 14-day observation period. The 0.05 mg/ml solution was well tolerated and at 0.1 mg/ml, the irritation was mild and reversible by the end of the 14-day observation period. The 0.2 or 0.3 mg/ml solutions produced more intense reactions that were not fully reversible. These latter skin reactions were associated with microscopic alterations of acanthosis with crust formation, inflammatory cell infiltrates, fibroplasia in the dermis, and superficial edema, and focal mineralization in animals receiving the 480 $\mu$A current. The degree of irritation was clearly related to the amount of current received. The saline and 240 $\mu$A current (Control) and the 0.3 mg/ml solution of bisphosphonate compound and no current (Group 7) were well tolerated and no skin reactions were induced in the animals. Under the conditions of this study, bisphosphonate compound induced primary skin reactions which were concentration-dependent.

B. A study was conducted to determine the effects of reversing current flow after delivery of a dosage of bisphosphonate compound The Group 1 animals (Control) received saline and a current setting of 800 μA for a 4 hour treatment time. Group 2 animals received 0.05 mg/ml bisphosphonate compound at 400 μA for 4 hours. Group 3 animals received 0.05 mg/ml at 400 μA for 4 hours followed by a reverse phase treatment at 800 μA for 1 hour. Group 4 animals received 0.05 mg/ml at 800 μA for 4 hours. Group 5 animals received 0.3 mg/ml at 400 μA for 1 hour. Group 6 animals received 0.3 mg/ml at 400 μA for 4 hours followed by a reverse phase treatment at 800 μA for 1 hour. Group 7 animals received 0.3 mg/ml at 800 μA for 1 hour. All animals received a single treatment followed by 14-day observation period. Skin reactions were noted at both concentrations and in all treated animals. At 0.05 mg/ml, erythema occurred with severity decreasing about 7 days after treatment, while edema was observed 2 to 3 days after treatment. Both were reversible by the end of the 14-day observation period. At 0.3 mg/ml, erythema was noted after treatment, with the severity progressing to marked edema over the entire treated area, a condition which was not reversible by the end of the 14-day observation period. These findings were associated with microscopic alterations of the skin and subcutaneous muscle layers at 0.05 mg/ml, and acanthosis/crust formation, inflammatory cell infiltrates, edema and fibroplasia in the dermis in all animals at 0.3 mg/ml, with focal epidermal necrosis with re-epithelialization in Groups 5 and 7, but not in Group 6 (additional reverse phase). The necrosis, edema and fibroplasia were slightly more pronounced in Group 7 (800 μA) than Group 5 (400 μA). Females exhibited a stronger tendency to inflammation than males. Under the conditions of this study, bisphosphonate compound induced primary skin reactions in albino rabbits, which were macroscopically concentration-dependent and microscopically concentration- and current-dependent and showed decreased effects due to the reverse phase.

We claim:

1. A bipolar iontophoretic drug delivery method for reducing delayed onset of local skin irritation comprising:

(a) applying a transdermal patch to the skin of a living body;
   (b) causing current to flow through the skin so as to iontophoretically deliver a bisphosphonate compound wherein said compound causes delayed onset of local skin irritation; and
   (c) reversing the direction of current flow through the skin for a reversal period of long enough duration to reduce the effects arising from the delayed onset of local skin irritation caused by the compound.

2. The method according to claim 1 wherein the current flow is at a level from about 0.01 to about 4 mA/cm$^2$.

3. The method according to claim 1 wherein a unit dosage of about 1 ng to about 100 mg is delivered through the skin during the delivery step.

4. The method according to claim 3 wherein the unit dosage is delivered over a time period of about 1 second to about 24 hours.

5. The method according to claim 1 wherein the reversed current flow is at a level from about 0.01 to about 4 mA/cm$^2$.

6. The method according to claim 1 wherein the reversed current is delivered over a time period of about 1 second to about 24 hours.

7. The method according to claim 1 wherein the pulsed or alternating current has a duty cycle less than 100%.

8. A method according to claim 1, wherein the direction of current flow is reversed after the desired dosage has been delivered.

9. The method of claim 1 wherein the bisphosphonate compound is 2-(imidazol-1-yl)-1-hydroxyethane 1,1-bisphosphonic acid.

10. The method according to claim 1 wherein the delivery or reverse current is continuous, pulsed current or alternating current.

11. The method according to claim 1 wherein the pulsed or alternating current has a frequency from 1 Hz–100 MHz.

12. The method according to claim 1 wherein the pulsed or alternating current has a waveform selected from the group consisting of a sine, square, triangular, saw tooth, and rectangular waveform.

* * * * *